United States Patent [19]

Schwab et al.

[11] Patent Number: 6,111,149
[45] Date of Patent: Aug. 29, 2000

[54] PROCESS FOR PREPARING ALCOHOLS AND/OR ALDEHYDES FROM OLEFINS

[75] Inventors: Peter Schwab, Bad Dürkheim; Arthur Höhn, Kirchheim; Rocco Paciello, Bad Dürkheim, all of Germany

[73] Assignee: BASF Aktiengesellschaft, Ludwigshafen, Germany

[21] Appl. No.: 09/214,521

[22] PCT Filed: Jul. 14, 1997

[86] PCT No.: PCT/EP97/03742

§ 371 Date: Jan. 7, 1999

§ 102(e) Date: Jan. 7, 1999

[87] PCT Pub. No.: WO98/03456

PCT Pub. Date: Jan. 29, 1998

[30] Foreign Application Priority Data

Jul. 20, 1996 [DE] Germany .......................... 196 29 369
Oct. 11, 1996 [DE] Germany .......................... 196 42 278

[51] Int. Cl.$^7$ ............................................. C07C 29/03
[52] U.S. Cl. ....................... 568/904; 556/482; 556/485
[58] Field of Search .................... 568/904, 908; 556/482, 485

[56] References Cited

U.S. PATENT DOCUMENTS 5,342,985  8/1994  Herrmann et al. .................... 556/482

FOREIGN PATENT DOCUMENTS 2 131 429  6/1984  United Kingdom .

OTHER PUBLICATIONS

Ind. Org. Chem., 4$^{th}$ Ed. 1994, pp 94–98.

J. Chem. soc., Chem. Commun. 1979, 330–331.

J. Am. Chem. Soc., vol. 118,1996, 100–110.

*Primary Examiner*—Johann Richter
*Assistant Examiner*—Sreeni Padmanabhan
*Attorney, Agent, or Firm*—Keil & Weinkauf

[57] ABSTRACT

Alcohols and/or aldehydes are prepared from olefins by cross-metathesis of olefins with alcohols having at least one double bond in the molecule and in which at least one hydroxyl is in the allyl position relative to a C═C double bond over catalysts of the formula (I)

$$XX^1LL^1Ru [sic]=CR^1R^2 \qquad (I)$$

with optional subsequent hydrogenation and/or isomerization, $R^1$ and $R^2$ being hydrogen or C-organic radicals with or without a heteroatom, X [sic] and $X^1$ [sic] being, independently, anionic ligands, and L [sic] and $L^1$ [sic] being, independently, neutral electron donor ligands.

11 Claims, No Drawings

PROCESS FOR PREPARING ALCOHOLS AND/OR ALDEHYDES FROM OLEFINS

This is a 371 of application No. PCT/EP97/03742, filed Jul. 14, 1997.

The present invention relates to a process for preparing alcohols and/or aldehydes from olefins by cross-metathesis of olefins with alcohols whose molecule includes at least one C=C double bond over catalysts of the formula (I)

$$X^1X^2L^1L^2Ru=CR^1R^2 \tag{I}$$

where $R^1$ and $R^2$ are hydrogen or an organic radical or a silyl radical;

$X^1$ and $X^2$ are anionic ligands; and $L^1$ and $L^2$ are neutral electron donor ligands;

with optional subsequent hydrogenation and/or isomerization.

Alcohols are valuable solvents or intermediates in organic syntheses, for example for preparing phthalates, acrylates or sulfonates. The aldehydes are used, for example, as intermediates for preparing the corresponding alcohols or acids.

A widely known and technically widespread reaction of olefins is catalytic olefin metathesis. A general overview of olefin metathesis is given, for example, by K. Weissermel and H. -J. Arpe in Industrielle Organische Chemie, 4th Edition, 1994, VCH Verlagsgesellschaft Weinheim, on pages 94 to 98.

Olefin metathesis corresponds formally to the exchange of the alkylidene groups of two olefin molecules. The reaction mechanism is usually formulated as metal-catalyzed scission of the double bonds in the original olefins and their subsequent reformation to give the products. The reaction is reversible. A general, formal equation which highlights the exchange of the substituents labeled $R^A, R^B, \ldots R^H$ but does not take into account the actual cis/trans stereochemistry is given below:

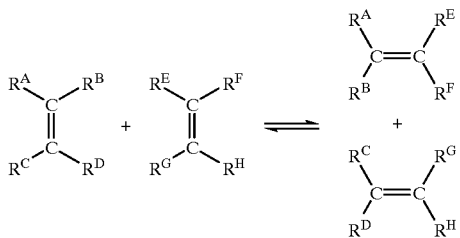

In general a distinction is made between self-metathesis, in which one olefin is converted to a mixture of two olefins differing in molar mass, an example being the transformation of two molecules of propene into one of ethene and one of 2-butene, and cross-metathesis, where two different olefins are converted to two new olefins, an example being the transformation of propene and 1-butene into ethene and pentene.

Metathesis reactions of functionalized olefins, that is those composed of additional elements as well as just carbon and hydrogen, are described much more rarely than metathesis reactions of pure hydrocarbon olefins. The most frequent examples relate to metathesis reactions of unsaturated ethers, esters and halides. For example, J. C. Mol and E. F. G. Woerlee in J. Chem. Soc., Chem. Commun., 1979, 330–331, describe the self-metathesis of ethers and formyl esters of unsaturated alcohols, with elimination of ethylene, over a tin-promoted rhenium oxide catalyst on an alumina support. U.S. Pat. No. 5,342,985 discloses the self-metathesis of ethers and esters of unsaturated alcohols over special organorhenium oxides.

GB-A-2 131 429 describes the self- or cross-metatheses, which it refers to generally as dismutation, of functionalized olefins. In accordance with all of the rest of the prior art, preference is given therein—on page 1, lines 49 to 52—to those oxygen substituents which are not hydroxyl. The suitability, in principle, of hydroxy-substituted olefins for metathesis reactions cannot be inferred from this document. α-Olefins α-substituted by hydroxyl, such as 4-penten-1-ol, in which olefins the hydroxyl group is further away from the double bond than if it were in the allyl position, can be metathesized with a specific ruthenium catalyst according to P. Schwab, R. H. Grubbs and J. W. Ziller, J. Am. Chem. Soc. 118 (1996) 100–110. α-Olefins of this kind with an ω hydroxyl group do not, however, display the high reactivity known for olefins having an allylic hydroxyl, especially not their propensity to allyl isomerization.

In the metathesis of an α-olefin with a hydroxyalkene where the oxygen substituent is further away from the double bond than if it were in the allyl position, at least two carbons are added onto the original α-olefin. On the basis of the common industrial α-olefins with a particular number of carbons, therefore, it is not possible by means of metathesis reactions with such hydroxyalkenes to obtain the alcohols or aldehydes having a carbon framework which originates from the original carbon framework of the α-olefin by addition of exactly one carbon. However, it is precisely such alcohols and aldehydes obtained by incorporating only one C atom which are of industrial interest. On the industrial scale they are obtained by oxo synthesis, in which α-olefins are reacted with a mixture of carbon monoxide and hydrogen to form aldehydes. This process of hydroformylation, however, is disadvantageous in that only α-olefins can be reacted and, after hydrogenation, only primary alcohols are obtainable. Furthermore, the ratio of n-products to the unwanted iso-products is unsatisfactory. Allyl alcohol cannot be obtained by hydroformylation and instead must be prepared from propene by an at least two-stage route.

It is an object of the present invention, therefore, to discover a process for preparing alcohols and/or aldehydes from α-olefins which makes it possible to prepare these products simply and with high selectivity while very largely avoiding the formation of iso-products. Furthermore, it should be possible to employ this process industrially in place of the oxo technology commonly used. By applying the process it should be possible, therefore, from the olefin feedstocks which are generally present in industry to prepare the alcohols and/or aldehydes which are generally required. To do this it is necessary for the carbon framework of the resulting alcohol and/or aldehyde to originate from the carbon framework of the olefin used by expansion by exactly one carbon. For increased flexibility, furthermore, the process should also permit the preparation of secondary and tertiary alcohols and should also enable the n-alcohols required industrially to be prepared from feedstocks other than linear α-olefins. Furthermore, the process should open up a simple route to preparing allyl alcohol.

We have found that this object is achieved by a process for preparing alcohols and/or aldehydes from olefins by cross-metathesis of olefins with alcohols whose molecule includes at least one C=C double bond over catalysts of the formula (I)

$$X^1X^2L^1L^2Ru=CR^1R^2 \tag{I}$$

where

R¹ and R² are hydrogen or an organic radical or a silyl radical;

X¹ and X² are anionic ligands; and

L¹ and L² are neutral electron donor ligands;
with optional subsequent hydrogenation and/or isomerization, which comprises using alcohols having at least one double bond in the molecule, in which at least one hydroxyl is in the allyl position relative to a C=C double bond.

The basis for the invention is the surprising finding that not only are the ruthenium compounds of the formula (I) stable to hydroxyl groups but also allyl alcohols, i.e. olefins having an allylic hydroxyl, which are usually highly reactive and isomerize very readily, can be metathesized over these catalysts.

Suitable starting materials for the novel process are olefins of the formula (II):

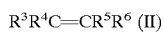

of generally 3 to 50 carbons, especially 3 to 30 carbons and, with preference, of 3 to 20 carbons. R³, R⁴, R⁵ and R⁶ independently can be hydrogen or an aliphatic, cycloaliphatic, aromatic, araliphatic or heteroaromatic radical, for example alkyl, alkenyl, alkynyl, cycloalkyl, cycloalkenyl, aryl, for example phenyl, alkaryl or aralkyl. The radicals can be substituted by other organic radicals and may also include heteroatoms, in the form for example of alkoxy substituents, ester groups, or amino or alkylamino functions. Heteroatoms such as oxygen, sulfur and nitrogen can also be part of an aromatic or cyclic radical. R³ with R⁴, and/or R⁵ with R⁶, can also be parts of a ring system, for example of 4 to 16 carbons, comprising R³, R⁴ and the double bond carbon attached to both of the latter, or R⁵, R⁶ and the double bond carbon attached to both of the latter. Mono- or polycyclic olefins, that is those in which R³ with R⁵ or R⁶, and/or R⁴ with R⁵ or R⁶, and in each case with the carbons of the double bond, form a ring system and where R³ with R⁴, and/or R⁵ with R⁶, may likewise be parts of ring systems comprising these radicals and, if appropriate, the corresponding carbons of the double bond as well, can also be converted to alcohols, with the opening of all of their rings which contain the double bond that is subject to metathesis.

Preferably, the olefins employed in the novel process are monosubstituted olefins having 3 to 20 carbons and at least one terminal C=C double bond. In these olefins R⁴, R⁵ and R⁶ are hydrogen. R³ is an organic radical of at least one carbon. Examples of α-olefins preferably used in the novel process are those in which R³ is linear saturated alkyl of one to 18 carbons, such as methyl, ethyl, propyl, butyl, pentyl, hexyl, heptyl, octyl, nonyl or decyl. R³ can also be saturated cycloalkyl of three to 18 carbons, for example cyclopentyl, cyclohexyl or cycloheptyl. R³ can also be branched saturated alkyl, such as 2-propyl, 2-butyl, 2-methyl-l-propyl, 1,1-dimethylethyl or any branched isomeric pentyl, hexyl, heptyl, octyl, nonyl or decyl. R³ can also be an unsaturated radical having one or more double and/or triple bonds which originates from the abovementioned saturated radicals by the formal removal of at least two hydrogens on adjacent carbons, examples being vinyl, propenyl, butenyl, 1-prop-2-enyl, l-but-2-enyl or 1-but-3-enyl. R³ can likewise be an aromatic radical, for example unsubstituted or substituted phenyl or 1- or 2-naphthyl.

It is likewise preferred to employ cycloolefins of 4 to 16 carbons in the novel process. In these olefins R³ with R⁵ or R⁶, and/or R⁴ with R⁵ or R⁶, and in each case with the carbons of the double bond, form a ring system. In addition to the double bond or bonds that are to be subjected to metathesis, this ring system may also include further double or triple bonds, or heteroatoms such as oxygen, sulfur or nitrogen. The cycloolefin may also be substituted by inert radicals. Examples of cycloolefins that can be used in the novel process are cyclopentene, cycloheptene, cyclooctene, cyclooctadiene, cyclododecene, cyclododecadiene, cyclododecatriene, dimeric cyclopentadiene, norbornene or norbornadiene.

The alcohols having at least one double bond in the molecule that are used in the novel process have at least one hydroxyl in the allyl position relative to the double bond, as illustrated in the formula (III). In the text below they are generally referred to as allylic alcohols.

R⁷, R⁸, R⁹, R¹⁰ and R¹¹ independently can be hydrogen or an aliphatic, cycloaliphatic, aromatic, araliphatic or heteroaromatic radical, for example alkyl, alkenyl, alkynyl, cycloalkyl, cycloalkenyl, aryl, for example phenyl, alkaryl or aralkyl. The radicals can be substituted by further organic radicals and may also include heteroatoms, for example in the form of alkoxy substituents, ester groups, amino functions or alkylamino functions. Heteroatoms such as oxygen, sulfur and nitrogen may also be part of an aromatic or cyclic radical. The radicals can be linked with one another and can be parts of a ring system having, for example, 4 to 12 carbons.

If an allylic alcohol is employed in the novel process whose radicals R¹⁰ and/or R¹¹ are not hydrogen but, for example, one or two alkyls or aryls, alkenyls or alkynyls or other substituents, then secondary or tertiary alcohols are formed. These secondary and tertiary alcohols cannot be prepared by oxo synthesis. It is an additional advantage of the novel process to be able to generate secondary and tertiary alcohols.

Owing to the high industrial requirement for primary alcohols, however, in the majority of cases R¹⁰ and R¹¹ will be hydrogen. R⁷, R⁸ and R⁹ independently of one another can be hydrogen or linear saturated alkyl of one to 10 carbons, such as methyl, ethyl, propyl, butyl, pentyl, hexyl, heptyl, octyl, nonyl or decyl. They may also be saturated cyclic alkyls of three to 10 carbons, for example cyclopentyl, cyclohexyl or cycloheptyl. They can also be branched saturated alkyls, such as 2-propyl, 2-butyl, 2-methyl-1-propyl, 1,1-dimethylethyl or any branched isomeric pentyl, hexyl, heptyl, octyl, nonyl or decyl. They can additionally be unsaturated radicals having one or more double and/or triple bonds, which originate from the abovementioned saturated radicals by the formal removal of at least two hydrogens located on adjacent carbons, examples being vinyl, propenyl, butenyl, 1-prop-2-enyl, 1-but-2-enyl or 1-but-3-enyl. They can similarly be aromatic radicals, for example unsubstituted or substituted phenyl or 1- or 2-naphthyl. All of these radicals can also contain inert substituents and/or heteroatoms. They can also be attached to the C atom of the allylic alcohol by way of heteroatoms, for example oxygen, nitrogen or sulfur, for instance in the form of alkoxy or alkylthio of one to 10 carbons.

Examples of such alcohols which are available industrially in very large quantities and are preferably employed in the novel process are 2-propen-1-ol (allyl alcohol) and 2-butene-1,4-diol (butenediol).

The alcohols can also be used as a mixture of at least two individual compounds, for example allyl alcohols with butenediol.

In a preferred embodiment of the invention, the olefin employed is ethylene and is reacted with butenediol to form allyl alcohol.

The metathesis of acyclic olefins with allylic alcohols produces both a new allylic alcohol and an olefin coupling product. The metathesis of α-olefins with allyl alcohol produces the desired metathesis product and ethylene as coupling product. The coupling product, for example ethylene, can be recovered in the novel process and can be used, for example, as a raw material for other processes. The metathesis of α-olefins with butenediol produces, in a first step, the desired metathesis product and allyl alcohol as coupling product. The latter reacts, in a second step, with the α-olefin to give the ultimate coupling product, ethylene. If use is made of longer-chain allylic alcohols whose radicals $R^7$ and/or $R^8$ are not hydrogen and/or of olefins whose double bond is not terminal, the coupling products are higher olefins. If mixtures of alcohols including at least one higher allyl alcohol and/or mixtures of olefins comprising at least one olefin whose double bond is not terminal are employed, the result is mixtures of coupling products and/or products which can be worked up by appropriate, known physical separation techniques, for example distillation.

In the metathesis of cyclic olefins with allylic alcohols the ring containing the olefinic double bond is opened. By subjecting cycloolefins to metathesis with allylic alcohols, therefore, an open-chain alcohol can be produced whose carbon framework comprises at least three carbons more than that of the cycloolefin employed. If a cycloolefin is reacted with butenediol by the process of the invention, an α,ω-dialcohol is produced. The novel process therefore opens up a new route for preparing linear alcohols based on cycloolefins instead of on α-olefins and thus provides greater flexibility in the preparation of alcohols.

The metathesis of ethylene with butenediol to form allyl alcohol of course produces only allyl alcohol, and no coupling product. The metathesis of ethylene with allyl alcohol does not of course lead to the synthesis of a new product that is not employed.

Catalysts used in the novel process are the ruthenium-alkylidene compounds disclosed in WO-A-93/20111, the ruthenium-based catalyst systems described in A. W. Stumpf, E. Saive, A. Demonceau and A. F. Noels in J. Chem. Soc., Chem. Commun. 1995, 1127–1128, or the ruthenium compounds disclosed by Schwab, Grubbs and Ziller, loc. cit., of the formula I.

$$X^1X^2LL^2Ru=CR^1R^2 \qquad (I)$$

In this formula $R^1$ and $R^2$ independently can be hydrogen or organic radicals or silyl radicals.

Examples of suitable organic radicals are alkyls, cycloalkyls or aryls of one to 20 carbons, alkenyls or alkynyls of 2 to 20 carbons, carboxylate radicals of one to 20 carbons, alkoxys or aryloxys of one to 20 carbons, alkenyloxys or alkynyloxys of 2 to 20 carbons, alkoxycarbonyls of 2 to 20 carbons, alkylthios of one to 20 carbons, or alkylsulfonyls or alkylsulfinyls of one to 20 carbons, all of which may themselves be substituted.

Suitable silyl radicals are silyls substituted by organic radicals. Examples of organic substituents are alkyls, cycloalkyls or aryls of one to 20 carbons, alkoxys or aryloxys of one to 20 carbons, or dialkyl- or diaryl- or alkylarylaminos.

Preferred catalysts are those ruthenium compounds of the formula (I) in which one of $R^1$ and $R^2$ is hydrogen. Particular preference is given to those in which one of $R^1$ and $R^2$ is hydrogen and the other is either aryl, for example phenyl, or alkenyl, for example 1-ethenyl substituted in position 2 by an organic, preferably aromatic radical such as phenyl, or is silyl, for example trialkylsilyl or triarylsilyl, such as trimethylsilyl or triphenylsilyl.

The aryls, for example phenyls, which may be present in the organic or in the alkenyl or in the silyl radical may themselves also be substituted, for example by one or more alkyls, cycloalkyls, aryls, alkoxys, alkylthios or aminos each of one to 6 C atoms. Examples of suitable substituents are methyl, ethyl, n-propyl, isopropyl, n-butyl, isobutyl, tert-butyl, cyclohexyl, cyclopentyl, phenyl, methoxy, ethoxy, methylthio, ethylthio, amino, methylamino or dimethylamino.

$X^1$ and $X^2$ are anionic ligands, for example independent halogens such as fluorine, chlorine, bromine or iodine, hydrogen, alkyl, cycloalkyl or aryl of one to 20 carbons, alkoxy or aryloxy of one to 20 carbons, alkyl- or aryldiketonates of 3 to 20 carbons, carboxylate radicals of one to 20 carbons, alkyl- or arylsulfonates of one to 20 carbons, alkylthios of one to 20 carbons, or alkylsulfonyl or alkylsulfinyl of one to 20 carbons. These radicals may themselves be substituted, for example by halogen, alkyl or alkoxy. Aryl is preferably phenyl or naphthyl.

$L^1$ and $L^2$ are neutral electron donor ligands. $L^1$ and $L^2$ can, for example, independently be phosphane or alkyl-, cycloalkyl- or aryl-substituted phosphines, or phosphites, phosphinites or phosphonites, arsane, stibane, ammonia, or alkyl-, cycloalkyl- or aryl-substituted arsanes, stibanes, ethers, aliphatic and aromatic amines, amides, mercaptans, thioethers, sulfoxides, carbon monoxide, nitrosyl or π-electron donors such as aromatic compounds, for example benzene substituted by organic radicals. Suitable organic radicals of a benzene ligand are inert organic radicals such as alkyls, alkenyls or alkoxys. One example of such an aromatic π-electron donor suitable for use as a neutral ligand is paramethylcumene.

These ligands $X^1$, $X^2$, $L^1$ and $L^2$ can be four individual ligands; however, it is also possible to use multidentate anionic ligands or multidentate neutral ligands. Multidentate ligands can also be used that have both anionic and neutral complexing functions, for example cyclopentadienyl, indenyl or fluorenyl radicals.

$X^1$ and $X^2$ are preferably halide ions. With particular preference, both $X^1$ and $X^2$ are chloride. $L^1$ and $L^2$ are preferably alkyl-, cycloalkyl- or aryl-, for example phenyl-, substituted phosphine ligands. With particular preference, $L^1$ and $L^2$ are cycloalkyl-substituted phosphine ligands, for example tris(cyclohexyl)phosphine or tris(cyclopentyl)phosphine.

The catalyst to be used in accordance with the invention can be prepared separately from the metathesis reaction and added to the reaction mixture, although it is also possible to prepare it in situ from its starting materials in the metathesis reaction mixture.

The novel process can in principle be conducted continuously or discontinuously. The novel process is generally conducted by bringing the alcohol into contact with the olefin and the catalyst in the reactor and working up the reaction mixture simultaneously or subsequently. Simultaneous workup is understood, for example, as the separation of at least some of at least one product or coupling product from the reaction mixture while the reaction is being carried out.

Metathesis reactions are equilibrium reactions, so that depending on the specific olefin, alcohol and catalyst used and on the chosen reaction conditions, such as pressure, temperature and feedstock concentrations, equilibrium is established at a particular position. To maximize the economic efficiency of the process regime, therefore, it is generally judicious to choose the reaction conditions such that the equilibrium lies as far as possible toward the side of the desired products. Furthermore, if the position of the equilibrium is not already particularly advantageous, it is generally economically judicious to shift the equilibrium toward the product side by removing the principal products and/or coupling products from the reaction mixture as quickly as possible, thereby maximizing the degree of conversion and the space-time yield. The equilibrium can if necessary be subjected to such shifting by, for example, removing the olefin coupling product which is formed in the metathesis alongside the desired alcohol product. Just as easily, however, the desired product itself could be removed from the reaction mixture, should the separation of this product be technically or economically more advantageous than that of the coupling product. It is likewise possible to remove principal product and coupling product from the reaction mixture simultaneously and then to separate them. The equilibrium can also be shifted, furthermore, by adding one starting material in excess, or by a combination of the two methods.

In the reaction of an $\alpha$-olefin with allyl alcohol and/or butenediol the coupling product formed is ethylene, which because of its high volatility is easy to remove from the reaction space, for example by distillation. This also applies to the higher olefin coupling products which are produced when use is made of olefins whose double bond is not terminal and/or of longer-chain allyl alcohols, provided their volatility is higher than that of the other product or products. If the principal products are substantially more volatile than the coupling products, it is also possible to remove the principal products from the reaction space, and thus withdraw them from the equilibrium, instead of the coupling products. If the volatilities of coupling product and principal product are alike, a mixture of the coupling products and principal products can be removed from the reaction space, for example by distillation, and then separated, for example by precision distillation, azeotropic distillation, with or without the addition of at least one auxiliary, or other methods of physical separation.

The process can be conducted, for example, in stirred reactors, loop reactors, cascades of stirred reactors or in tube reactors. For separating principal products, coupling products and/or byproducts in the plant for implementing the novel process, these reactors are equipped with separation devices such as, for example, distillation columns, phase separators, membrane separation devices, absorption devices or equivalent apparatus.

In the case of discontinuous implementation of the novel process a mixture of the olefin feedstock, the alcohol feedstock and the catalyst, or a solution of the catalysts, is introduced into a reactor for the reaction. In this context, the catalyst or catalyst solution is advantageously added to a mixture of the olefin feedstock used and of the alcohol feedstock, with or without a solvent. As soon as a satisfactory degree of conversion has been reached, the reaction mixture is worked up and the products are isolated. Alternatively, if the position of the equilibrium is unsatisfactory, removal of the principal products and/or coupling products from the reaction space, and thus from the equilibrium, can be commenced after or even during the addition of the catalyst or catalyst solution. This can be done, for example, by distilling a stream of material withdrawn continuously from the reactor and recycling the unreacted feedstocks into the reaction space. The catalyst which remains in the distillation bottoms can be used again in a new batch.

With continuous implementation of the novel process, the catalyst or a catalyst solution, the olefin feedstock and the alcohol feedstock and [sic] are introduced continuously into the reaction space, which may also contain a solvent. It may be advantageous to add the components not in pure form but, at least in part, as a mixture of at least two components, for example a mixture of the olefin and the alcohol, for example when a mixture of unreacted starting materials is available from the workup of the reaction products of the novel process, or when a composition suitable for use in the novel process is available from other sources. Principal and coupling products are removed continously from the reaction space. This can be done, for example, by distilling a stream of material withdrawn continuously from the reactor and recycling the unreacted feedstocks and, if appropriate, the solvent, to the reaction. The catalyst which remains in the distillation bottoms can likewise be recycled to the reaction. If necessary, for example if deactivation occurs, the catalyst can be reprocessed before being recycled, or replaced at least in part by fresh catalyst.

Rather than by distillation the principal products and/or coupling products can also be separated, for example, by membrane techniques, absorption techniques or by a combination of the methods.

In addition to the desired products and the coupling products obtained, the novel process normally produces byproducts as well. These byproducts are, for example, the higher olefins formed by the self-metathesis of the olefin used. If, for example, an $\alpha$-olefin is used, it may be converted to a symmetrical olefin with the double bond in the center of its carbon framework by a metathesis reaction with itself in which ethene is eliminated. Although these higher olefins are likewise capable of metathesis with the allylic alcohols employed, they generally react at a lower rate than $\alpha$-olefins, so that in the metathesis of $\alpha$-olefins their formation is undesirable from the standpoint of an economically optimum space-time yield and is avoided by very rapid removal of the desired products from the equilibrium. The byproducts can be removed from the reaction mixture together with the desired products and the coupling products, for example by distillation. Alternatively, they can be removed by a discrete separation technique for the byproducts, for example by distilling a component stream removed specifically for this purpose from the reaction space and recycling all constituents other than the byproducts back to the reaction space. When the process is carried out continuously their removal is advisable, since otherwise they steadily accumulate in the reaction mixture.

The catalyst can be used in solid form or, preferably, in an inert organic solvent, for example aliphatic hydrocarbons of 4 to 20 carbon atoms which are liquid under the reaction conditions, such as butane, pentane, hexane or heptane, chlorinated hydrocarbons such as methylene chloride, chloroform or carbon tetrachloride, or aromatic hydrocarbons such as benzene, toluene or xylenes. Preference is given to using methylene chloride or toluene. The reaction itself can be conducted using a solvent, in addition to any solvent used for the catalyst, or in general can be carried out, preferably, without solvent in order to increase the space-time yield, with the exception of any solvent used for the catalyst. If a solvent is used, it can preferably be the same as or different from that used in the solution of the catalyst. If the alcohol used is 2-butene-1,4-diol in relatively high concentrations, it may be advantageous to add a solubilizer. Examples of solubilizers that can be used are acetone and/or ethylene glycol dibutyl ether.

The appropriate reaction temperature is generally below 200° C. To avoid secondary reactions it is in most cases advantageous to conduct the reaction at below 120° C. With preference, the novel process is carried out below 80° C. The practicable temperature range for the novel process is limited at its lower end only by the availability of economically satisfactory space-time yields. In general it is useful to choose temperatures above −20° C., preferably above 0° C. and, with particular preference, above +20° C.

The reaction pressure to be employed in the novel process is not generally critical. It can, for example, be a superatmospheric pressure of up to 325 bar, preferably not more than 10 bar and, in particular, not more than 2 bar. In general the absolute reaction pressure will be above 20 mbar, preferably above 0.1 bar and, in particular, above 0.5 bar.

The molar ratio of the olefin employed to the alcohol employed can in principle be varied within very wide limits. Because of the increasing formation of products of the self-metathesis of olefin or alcohol it is advantageous to establish this ratio in the range from 100:1 to 1:100. It is most often advantageous to establish it in the range from 10:1 to 1:10. This ratio is preferably from 2:1 to 1:2 and with particular preference from 1.5:1 to 1:1.5. The molar ratio of olefin employed to catalyst is generally from 10:1 to 20,000:1, preferably from 50:1 to 8000:1, and with particular preference from 100:1 to 5000:1.

The reaction is generally at an end after a period of from one minute to five hours.

The products of the metathesis reaction between an olefin and an allylic alcohol are, of course, again an olefin and an allylic alcohol or, if a cyclic olefin has been used, the product is in turn an allylic alcohol having a double bond in the o position relative to the new allyl unit.

Where the novel process produces an olefin, it is separated from the allylic alcohol and is obtained as coupling product. The olefin coupling product can subsequently be used in any other process in which olefins are the feedstock, examples being polymerization, oxidation, thermal or catalytic cracking, or metathesis reactions.

The allylic alcohol prepared in the course of the novel process in the stage of metathesis reaction, without taking into account in any way the possible cis/trans isomerism, has the formula (IV):

$$R^3R^4C=CR^9-C(OH)R^{10}R^{11} \quad (IV),$$

where $R^3$, $R^4$, $R^9$, $R^{10}$ and $R^{11}$ are as defined above.

These alcohols can in principle be used as they are. Normally, however, they will be hydrogenated in order to convert the allylic double bond to a single bond. This can be done by any known hydrogenation technique which can be used to convert C=C double bonds to C—C single bonds without reducing hydroxyl groups. If desired, further double bonds which may be present in $R^3$, $R^4$, $R^9$, $R^{10}$ and $R^{11}$, for example if cyclic olefins are used, can be hydrogenated as well simultaneously in this hydrogenation step. For example, alcohols of the formula (IV) can be reacted with hydrogen in the presence of heterogeneous catalysts comprising metals of subgroup VIII. Suitable catalysts are, for example, platinum or palladium on inert supports such as porous silica or porous alumina.

If at least one of $R^{10}$ and $R^{11}$ in the allylic alcohol of the formula (IV) is hydrogen it is also possible, by rearrangement of the allylic double bond and the automatically ensuing keto/enol tautomerization, to prepare aldehydes or ketones from the allylic alcohol. Aldehydes are formed if both $R^{10}$ and $R^{11}$ are hydrogen; if only one of them is hydrogen, then ketones are formed. This rearrangement is catalyzed, for example, by certain ruthenium compounds or metallic ruthenium on an inert alumina support. Processes which make use of such rearrangement under ruthenium catalysis and which can also be employed in the novel process for further processing of the allylic alcohol to aldehydes or ketones are known, for example, from U.S. Pat. No. 4,117,016, WO-A-91/03449 or WO-A-95/19334.

The alcohols or aldehydes produced in this way as the end product from an α-olefin by reaction with allyl alcohol correspond to the products originating from an oxo synthesis with or without subsequent hydrogenation, using the same olefin, with the difference that with the novel procedure the fraction of unwanted iso-aldehydes and iso-alcohols, which is automatically obtained with the oxo synthesis, is not produced. In addition, in contradistinction to the oxo synthesis, the desired aldehydes and alcohols can be obtained from cyclic olefins too and if allylic alcohols are used whose $R^{10}$ and Rll include at least one radical which is not hydrogen are employed the novel process can be used to prepare secondary and tertiary alcohols or ketones as well.

EXAMPLES

Examples 1 to 6

A mixture of 5 ml of olefin and an equimolar amount of allyl alcohol was charged to a Schlenk tube, and at room temperature a solution of $RuCl_2(=CHPh)(PCy_3)_2$ (where Ph is phenyl and Cy is cyclohexyl) in $CH_2Cl_2$ was added. The molar ratios of olefin, alcohol and catalyst were 100:100:1. In each case within a few minutes a characteristic color change of the solution from violet through claret to orange was observed. The ethene formed escaped through a bubble counter. After a reaction time of 2 h, samples were taken and analyzed by gas chromatography. The olefins used, the conversions of olefin achieved, and the measured selectivities for alcohol from the cross-metathesis and for byproducts from the self-metathesis of the olefin are reproduced in Table 1 below.

TABLE 1

| Ex. No. | Olefin | Conversion [mol-%] | Selectivity for alcohol [mol-%] | Selectivity for byproducts [mol-%] |
|---|---|---|---|---|
| 1 | 1-hexene | 16% | 74% heptenol | 25% decene |
| 2 | 1-octene | 12% | 72% nonenol | 28% tetradecene |
| 3 | 1-nonene | 13% | 72% decenol | 26% hexadecene |
| 4 | 1-decene | 12% | 72% undecenol | 27% octadecene |
| 5 | 1-undecene | 12% | 71% dodecenol | 27% eicosene |
| 6 | 1-dodecene | 11% | 74% tridecenol | 26% doeicosene |

Example 7

An equimolar mixture of 25 ml of cyclopentene and 19.5 ml of allyl alcohol (0.29 mol of each) was charged to a Schlenk tube, and at room temperature a solution of 239 mg (0.29 mmol) of $RuCl_2(=CHPh)(PCy_3)_2$ in $CH_2Cl_2$ was added. In addition to a vigorous evolution of gas (ethene escaped via a bubble counter), the abovementioned characteristic color change of the solution was observed within a few minutes. After a reaction time of 30 minutes a sample was removed and analyzed by gas chromatography. The degree of conversion of cyclopentene was 83 mol-% and the selectivities for the individual reaction products, in mol-%, were:

2,7-octadien-1-ol: 59;
2,7,12-tridecatrien-1-ol: 27;

2,7,12,17-octadecatetraen-1-ol: 7;
2-butene-1,4-diol: 6;
1,6-heptadiene: 1.

Example 8

An equimolar mixture of 25 ml of cis-cyclooctene and 15 ml of allyl alcohol (0.19 mol of each) was charged to a Schlenk tube, and at room temperature a solution of 156 mg (0.19 mmol) of $RuCl_2(=CHPh)(PCy_3)_2$ in $CH_2Cl_2$ was added. In addition to a gradual evolution of gas (ethene escaped via a bubble counter), the abovementioned characteristic color change of the solution was observed within a few minutes. After a reaction time of 2 h a sample was removed and analyzed by gas chromatography. The degree of conversion of cyclooctene was 33 mol-% and the selectivities for the individual reaction products, in mol-%, were:
2,10-undecadienol-1-ol [sic] 76;
2,10,18-nonadecatrien-1-ol 4;
2-butene-1,4-diol 19;
1,9-decadiene 1.

Example 9

An equimolar mixture of 25 ml of 1,5-cyclooctadiene and 13.9 ml of allyl alcohol (0.2 mol of each) was charged to a Schlenk tube, and at room temperature a solution of 250 mg (0.3 mmol) of $RuCl_2(=CHPh)(PCy_3)_2$ in $CH_2Cl_2$ was added. In addition to a vigorous evolution of gas (ethene escaped via a bubble counter), the abovementioned characteristic color change of the solution was observed within a few minutes. After a reaction time of 2 h a sample was removed and analyzed by gas chromatography. The degree of conversion of cyclooctadiene was 48 mol-% and the selectivities for the individual reaction products, in mol-%, were:
2,6,10-undecatrien-1-ol 65;
2,6,10,14,18-nonadecapentaen-1-ol 5;
2-butene-1,4-diol 8;
1,5,9-decatriene 22.

Example 10

An equimolar mixture of 25.0 ml of cyclopentene and 23.9 ml of 2-butene-1,4-diol (0.29 mol of each) in 5 ml of ethylene glycol dibutyl ether was charged to a Schlenk tube, and at room temperature a solution of 239 mg (0.29 mmol) of $RuCl_2(=CHPh)(PCy_3)_2$ in $CH_2Cl_2$ was added. The abovementioned characteristic color change of the solution was observed within a few minutes. After a reaction time of 30 minutes a sample was removed and analyzed by gas chromatography. The degree of conversion of cyclopentene was 24 mol-% and the selectivities for the individual reaction products, in mol-%, were:
2,7-nonadiene-1,6-diol 64;
2,7,12-tetradectriene-1,13-diol [sic] 36.

Example 11

40.0 g of butenediol were charged to a pressure vessel, and at room temperature a solution of 400 mg of $RuCl_2(=CHPh)(PCy_3)_2$ (where Ph is phenyl and Cy is cyclohexyl) in 12 ml of a mixture of equal parts by volume of $CH_2Cl_2$ and N-methylpyrrolidone was added. Then ethylene was injected at room temperature up to a pressure of 30 bar, the reaction mixture was heated to 50° C. and the pressure was raised to 75 bar by further supply of ethylene. In the course of 2 hours, the pressure, which fell during the reaction, was kept at 75 bar by further addition of ethylene. The pressure vessel was then let down and the discharged reaction mixture was analyzed by gas chromatography. Evaluation of the gas chromatogram by area % indicated a butenediol conversion of 58% and a selectivity for allyl alcohol of 87%.

We claim:

1. A process for preparing alcohols and/or aldehydes from olefins by cross-metathesis of olefins with alcohols whose molecule includes at least one allylic C=C double bond over catalysts of the formula (I)

$$X^1X^2L^1L^2Ru=CR^1R^2 \qquad (I)$$

where $R^1$ and $R^2$ are hydrogen or an organic radical or a silyl radical;

$X^1$ and $X^2$ are anionic ligands; and $L^1$ and $L^2$ are neutral electron donor ligands;

with optional subsequent hydrogenation and/or isomerization, which comprises using alcohols having at least one double bond in the molecule, in which at least one hydroxyl is in the allyl position relative to a C=C double bond.

2. A process as claimed in claim 1, wherein a monosubstituted olefin having at least one terminal C=C double bond is used.

3. A process as claimed in claim 2, wherein a linear olefin having a terminal C=C double bond is used.

4. A process as claimed in claim 1, wherein a cyclic olefin having at least one C=C double bond is used.

5. A process as claimed in claim 4, wherein a monocyclic olefin having a C=C double bond is used.

6. A process as claimed in claim 1, wherein as alcohol having at least one double bond in the molecule use is made of allyl alcohol (2-propen-1-ol) and/or butenediol (2-butene-1,4-diol).

7. A process as claimed in claim 1, wherein allyl alcohol is prepared by metathesis of ethylene with but-2-ene-1,4-diol.

8. A process as claimed in claim 1, wherein a metathesis catalyst of the formula (I) is used in which X and $X^1$ are halogens, L and $L^1$ are substituted phosphines, $R^1$ is aryl and $R^2$ is hydrogen.

9. A process as claimed in claim 1, wherein the metathesis is conducted at from −20 to +120° C.

10. A process as claimed in claim 1, wherein the molar ratio of the olefin employed to the alcohol employed is in the range from 100:1 to 1:100.

11. A process as claimed in claim 1, wherein the metathesis is conducted under a pressure of from 0.5 to 325 bar.

* * * * *